United States Patent [19]

Hussein et al.

[11] Patent Number: 5,035,882
[45] Date of Patent: Jul. 30, 1991

[54] COMBINATION OF FORMATE ESTERS AND PEPPER-LIKE CONSTITUENTS AS AN ORALLY-CONSUMABLE CHLOROFORM SUBSTITUTE

[75] Inventors: Mamoun M. Hussein, Mountain Lakes; Shirley A. Barcelon, Randolph; Donald M. Lynch, Flemington, all of N.J.

[73] Assignee: Warner-Lambert Company, Morris Plains, N.J.

[21] Appl. No.: 508,758

[22] Filed: Apr. 12, 1990

[51] Int. Cl.$^5$ .............. A61K 7/16; A61K 7/26; A61K 9/68; A61K 35/78
[52] U.S. Cl. .................. 424/58; 424/440; 424/441; 426/3; 426/533; 426/537; 426/650; 426/651; 514/974
[58] Field of Search .............. 424/58, 440, 441; 426/3, 533, 537, 650; 514/974

[56] References Cited

U.S. PATENT DOCUMENTS

| | | | |
|---|---|---|---|
| 4,082,841 | 4/1978 | Pader | 424/52 |
| 4,131,687 | 12/1978 | Mussinan et al. | 426/538 |
| 4,153,680 | 5/1979 | Seybert | 424/49 |
| 4,195,099 | 3/1980 | Sprecker et al. | 426/536 |
| 4,198,393 | 4/1980 | Yoshida et al. | 424/49 |
| 4,282,205 | 8/1981 | Sprecker et al. | 424/49 |
| 4,296,137 | 10/1981 | Boden | 426/534 |
| 4,374,824 | 2/1983 | Wahmi | 424/58 |
| 4,409,257 | 10/1983 | Deline | 426/651 |
| 4,454,111 | 6/1984 | Boden et al. | 424/58 |
| 4,521,634 | 6/1985 | Fujioka et al. | 568/665 |
| 4,849,238 | 7/1989 | Walkabayashi et al. | 426/650 |

OTHER PUBLICATIONS

Zilberboim et al, J. Food. Sci. 51(5): 1301–1306 (1986).

*Primary Examiner*—Shep K. Rose
*Attorney, Agent, or Firm*—Carl W. Battle

[57] ABSTRACT

The combination of pepper-like constituents, such as piperine, and volatile formate esters, such as ethyl formate, is useful as a substitute for chloroform in pharmaceutical, oral hygiene and confectionery compositions.

24 Claims, No Drawings

COMBINATION OF FORMATE ESTERS AND PEPPER-LIKE CONSTITUENTS AS AN ORALLY-CONSUMABLE CHLOROFORM SUBSTITUTE

SUMMARY OF THE INVENTION

This invention relates to novel compositions comprising a combination of one or more pepper-like constituent(s) and one or more volatile formate ester(s) which are useful as a chloroform substitute in a wide variety of pharmaceutical, oral hygiene and confectionery products. The compositions specifically comprise from about 0.01% to about 1.0% by weight of pepper-like constituent(s) and from about 5.0% to about 99.5% by weight of volatile formate ester(s). The pepper-like constituents are preferably selected from the group consisting of piperine, iso-piperine, chavicine, iso-chavicine, capsaiacin, capsicum extract, capsicum oleoresin, zingerone, mustard oil, horseradish extract, hot pepper oil, hot pepper extract and mixtures thereof. The volatile formate esters are preferably $C_1$–$C_4$ alkyl formate esters, such as ethyl formate, methyl formate, propyl formate, and isopropyl formate, and they preferably have a boiling point of less than about 80° C.

The compositions of this invention are useful in a variety of products such as cough medicines, cold medicines, mouthwashes, toothpastes, lozenges and chewing gums as a replacement for chloroform. The compositions of this invention have essentially all of the taste and mouthfeel characteristics of chloroform and they are relatively non-toxic, non-carcinogenic, non-anesthetic and safer to handle and process.

BACKGROUND OF THE INVENTION AND INFORMATION DISCLOSURE

Many pharmaceutical, oral hygiene and food products have incorporated chloroform as a flavoring aid because of its unique flavor characteristics. The flavor characteristics of chloroform can generally be described as a sweet, cooling, fizzy, tingly and slight burning effect. These flavor characteristics of chloroform are especially desirable in orally-administered cough-/cold medicines, mouthwashes, mouth sprays, toothpastes, chewing gums and candy breath fresheners.

However, chloroform has been identified as a carcinogen, and it has been banned by the U.S. Food and Drug Administration from use in drug, cosmetic and food products since 1976. There have been considerable efforts over the past 10 years to find a substitute for chloroform for use in food and drug applications. Nevertheless, none of the chloroform substitutes that have been developed over the past decade completely mimics the sensory attributes and flavor characteristics of chloroform.

U.S. Pat. No. 4,131,687 describes compositions for enhancing the flavor of consumable materials using at least one $C_{10}$-terpene alkyl, alkenyl, haloalkenyl, and alkynyl ether and diether. The compositions of the '687 patent are described as being suitable for use with a large number of flavoring adjuvants, such as, inter alia, ethyl formate or piperine. The '687 patent does not disclose flavoring compositions which are useful as a substitute for chloroform.

U.S. Pat. No. 4,195,100 describes the use of 2-oxabicycloocatane derivatives to enhance or augment the flavor of food ad medicinal products. These oxabicyclooctane derivatives augment or enhance eucalyptus, herbaceous, blueberry-like, piney, lime-like, clove, banana-like, woody, oriental-like, spicy, black pepper and floral flavor characteristics with stringent, biting and bitter effects. These oxabicyclooctane derivatives are useful with a large variety of flavoring adjuvants, such as ethyl formate or piperine. The '100 patent does not disclose flavoring compositions which are useful as a substitute for chloroform.

U.S. Pat. No. 4,198,393 describes the use of cyclic acetals of 2-methyl-2-pentenal in foodstuffs, chewing gums, toothpastes or medicinal products to produce sweet, fruity, goose berry, green, spearmint-like, aniseed, licorice, floral and herbal flavor characteristics. These may also be used with a large variety of flavorants, such as ethyl formate, piperine and many others. The '393 patent does not teach or suggest flavoring compositions which are useful as a replacement for chloroform.

U.S. Pat. No. 4,282,205 discloses that certain 2,4,6-trimethylcyclohexenemethanol derivatives are capable of augmenting or enhancing a variety of flavors and fragrances of various consumable materials. A large variety of other flavorants may be included such as ethyl formate, piperine and many others. However, the '205 patent does not disclose or suggest flavoring compositions which are useful as a chloroform substitute.

U.S. Pat. No. 4,296,137 discloses that 1-ethoxy-1-ethanol acetate is capable of imparting, augmenting or enhancing a variety of flavors and fragrances to various consumable materials. Other flavorants useful therewith include ethyl formate, piperine and many others. Flavorings as a substitute for chloroform are not disclosed or suggested by the '137 patent.

U.S. Pat. No. 4,521,634 relates to ether carbinols which are capable of augmenting or enhancing the aroma and/or taste of consumable materials, including foodstuffs, chewing gums, toothpastes, medicinal products and tobaccos. These ether carbinols are described at col. 66, lines 25–48 as capable of extending the fresh after-taste without having an effect similar to that of chloroform and without the use of chloroform. Thus, the '634 patent does not disclose or teach flavoring compositions which are useful as chloroform substitutes and which has essentially all of the flavoring effects of chloroform.

U.S. Pat. No. 4,454,111 discloses that prenyl methyl carbonates are useful in flavoring foodstuffs, chewing gums, toothpastes and medicinal products. Cooling and "chloroform-like" nuances may be provided by the utilization of these prenyl methyl carbonates. Other flavorants may also be used with these prenyl methyl carbonates.

Methyl formate and iso-propyl formate are described by Steffen Arctander, *Perfume and Flavor Chemicals*, 1969 as being occasionally used in place of chloroform to produce a flavor-burst or warm bite. However, Arctander does not teach the formate esters in combination with pepper-like constituents to obtain essentially all of the taste and sensory characteristics of chloroform.

None of the flavoring compositions known in the prior art provides substitutes for chloroform which exhibit essentially all of the flavor and taste characteristics of chloroform. It is the object of the present invention to provide a flavoring substitute for chloroform which has comparable flavor and taste characteristics as chloroform in essentially every respect. It is a further object of the present invention to provide a flavoring composition which is useful as a substitute for chloroform and which is relatively non-toxic and non-carcinogenic. It is an even further object of this invention to provide novel, orally-consumable compositions comprising a combination of pepper-like constituents and one or more volatile formate ester(s) which exhibit a sweet, cooling, tingly and slightly burning and biting taste.

DETAILED DESCRIPTION

The present invention involves novel flavoring compositions which are useful as a direct substitute for chloroform in a variety of pharmaceutical, medicinal, oral hygiene and confectionery products. These flavoring compositions exhibit essentially all of the taste, flavor and mouthfeel characteristics of chloroform, and they are relatively non-toxic, non-carcinogenic and non-anesthetic.

The compositions of this invention comprise a combination of one or more pepper-like constituents and one or more volatile formate esters. The compositions preferably comprise by weight from about 0.01% to about 1.0% of pepper-like constituents; more preferably from about 0.05% to about 0.7%; and most preferably from about 0.1% to about 0.65%. Further, the compositions preferably comprise by weight from about 5% to about 99.5% of volatile formate ester(s); more preferably from about 10% to about 70%; and most preferably from abut 20% to about 50%.

The pepper-like constituents useful according to the present invention are those orally-consumable materials which have pungent and biting taste characteristics similar to that of pepper. Preferably the pepper-like constituents are selected from the group consisting of piperine, iso-piperine, chavicine, iso-chavicine, capsaiacin, capsicum extract, capsicum oleoresin, zingerone, mustard oil, horseradish extract, hot pepper oil, hot pepper extract, and mixtures thereof. The most preferred pepper-like constituent for use in this invention is piperine.

Piperine is a known flavorant which has the chemical name 1-[5-(1,3-benzodioxol-5-yl)-1-oxo-2,4-pentadienyl]piperidine. It can be represented by the following chemical formula:

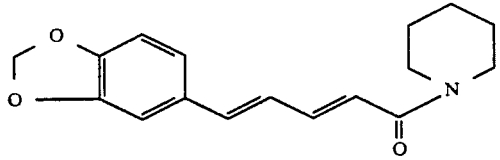

Piperine is generally isolated from black pepper through an extraction process.

The volatile formate esters useful in this invention include those formate esters which are orally-consumable and which have a boiling point of less than about 80° C. The volatile formate esters are preferably $C_1$-$C_4$ alkyl formate esters. More preferably the volatile formate esters are selected from the group consisting of ethyl formate, methyl formate, propyl formate, iso-proply formate and mixtures thereof. Ethyl formate is the most preferred of the volatile formate esters.

In preparing the flavoring compositions of this invention, the pepper-like constituents and formate esters are simply blended or mixed together using conventional techniques. The pepper-like constituents and formate esters can be blended into an acceptable solvent, such as ethyl alcohol, and can include other optional ingredients, such as sweeteners. A preferred composition of this invention comprises by weight from about 0.1% to about 0.7% piperine, from about 20% to about 99.4% ethyl formate, from about 0% to about 42% glycerine and from about 0% to about 65% ethyl alcohol. A more preferred embodiment comprises by weight about 0.62% piperine and about 99.38% ethyl formate. Another more preferred embodiment comprises by weight about 0.22% piperine, about 35.6% ethyl formate and about 64.18% ethyl alcohol. The most preferred embodiment comprises by weight about 0.13% piperine, about 20.77% ethyl formate, about 41.65% glycerin and about 37.45% ethyl alcohol.

The flavoring compositions of the present invention can be uniformly incorporated into a variety of orally-consumable materials as a chloroform substitute to improve the taste thereof. The term "orally-consumable" as used herein means foodstuff, pharmaceutical and medicinal products which are swallowed, consumed or ingested, as well as those which are simply placed in the mouth and subsequently discarded. These products include pharmaceuticals such as cough syrups, cough drops, cold and allergy medicines and chewable medicinal tablets. The medicinal products can be oral hygiene compositions such as mouthwashes, mouth sprays, toothpastes and chewing gums. The foodstuffs include beverages and confectionery materials such as candies and gums.

Pharmaceutical compositions prepared according to this invention preferably comprise from about 0.05% to about 6% by weight of the novel flavoring composition of this invention as a substitute for chloroform. The flavoring compositions of this invention are preferably used in cough or cold medicines as a chloroform substitute. A particularly preferred cough medicine comprises by weight about 11.4 parts sodium citrate, about 3 parts sodium saccharin, about 2 parts sodium benzoate, about 700 part glucose, about 39.3 parts glycerin, about 2.2 parts citric acid, about 27 parts ammonium chloride, about 201 parts sucrose, about 2.8 parts diphenhydramine hydrochloride, about 0.22 parts menthol, about 52.4 parts ethyl alcohol, about 8.1 parts flavoring and about 25 parts of said chloroform substitute flavoring composition.

Oral hygiene compositions prepared according to the present invention preferably comprise from about 0.01% to about 5% of this invention as a substitute for chloroform. Particularly preferred oral hygiene compositions are mouthwashes, toothpastes, chewing gums and candy breath fresheners.

Confectionery products, such as candy lozenges, prepared according to this invention comprise from about 0.05% to about 2% by weight of the flavoring composition of the present invention as a substitute for chloroform.

The compositions of this invention can include other optional ingredients such as stabilizers, thickeners, surface active agents, conditioners and flavorants, provided that these optional ingredients are orally-consumable, non-toxic and acceptable as to taste characteristics. Stabilizer compounds include preservatives, e.g. sodium chloride, antioxidants, e.g. calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4- methyl phenol), propyl gallate and the like and sequestrants, e.g. citric acid.

Thickener compounds include carriers, binders, protective colloids, suspending agents, emulsifiers and the like, e.g., agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acid, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta-dimethylacrolein, methyl-n-amyl ketone, n-hexenal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl isobutyrate, ethyl isovalerate, ethyl laurate, ethyl myristate, ethyl alpha-methylbuytrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; terpene hydrocarbons such as myrcene, caryophyllene, 1-phellandrene, p-cymene, 1-alpha-pinene, beta-pinene, dihydrocarveol; pyrazines such as 2,3-dimethylpyrazine, 2,5-dimethylpyrazine, 2,6-dimethyl-pryrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils and extracts such as jasmine absolute, cassia oil, cinnamon bark oil, rose absolute, orris absolute, oil of cubeb, oil of coriander, oil of pimento leaf, oil of patchouli, oil of nutmeg, lemon oil, safron oil, Bulgarian rose, yara yara and vanilla; lactones such as gamma-nonalactone; sulfides, e.g., methyl sulfide and other materials such as maltol, acetoin and acetals (e.g., 1,1-diethoxyethane, 1,1-dimethoxyethane and dimethoxymethane), and piperidine.

The following examples are presented to further demonstrate this invention. The examples are intended to be illustrative and are not intended in a limitative sense. All parts and percentages are on a weight basis unless otherwise indicated.

EXAMPLE I

Flavoring compositions falling within the scope of this invention were prepared by uniformly mixing the ingredients in the amounts shown in Table I below:

TABLE I

| Ingredient: | Sample: A | B | C |
|---|---|---|---|
| Ethyl Formate | 20.77% | 99.38% | 35.6% |
| Piperine | 0.13% | 0.62% | 0.22% |
| Ethyl Alcohol | 37.45% | 0.0% | 64.18% |
| Glycerin | 41.65% | 0.0% | 0.0% |

EXAMPLE II

The flavoring compositions prepared in Example I were each admixed with toothpaste as a substitute for chloroform and evaluated for taste characteristics. The toothpastes containing the flavoring compositions of this invention were compared to toothpaste containing chloroform. The specific formulations for these toothpaste samples are presented in Table II below:

TABLE II

| Ingredient: | Sample: D | E | F | G(Control) |
|---|---|---|---|---|
| Mint Flavored Toothpaste | 99.25% | 99.89% | 99.55% | 99.33% |
| Flavoring Composition Sample A | 0.75% | — | — | — |
| Flavoring Composition Sample B | — | 0.11% | 0.045% | — |
| Flavoring Composition Sample C | — | — | — | 0.67% |

Samples D, E, and F, falling within the scope of this invention, were each judged to simulate the odor, diffusivity and taste of Sample G, which contained chloroform. Sample D was judged to be equivalent to Sample G in the above characteristic, while Sample E and Sample F were judged to be better.

EXAMPLE III

A cough syrup base formulation was prepared as follows:

| Ingredient | Amount/Liter |
| --- | --- |
| Sodium Citrate | 11.40 grams |
| Sodium Saccharin | 3.00 grams |
| Sodium Benzoate | 2.00 grams |
| Liquid Glucose | 700.00 grams |
| Glycerin | 39.30 grams |
| Citric Acid | 2.20 grams |
| Ammonium Chloride | 27.00 grams |
| Sucrose | 201.00 grams |
| Diphenhydramine Hydrochloride | 2.80 grams |
| Menthol | 0.22 grams |
| Ethyl Alcohol (USP 95%) | 52.40 ml. |
| Flavorants (Caramel/ Ponceau 4R/Raspberry) | 8.10 grams |

Diluted with deionized water to 1 liter.

A cough syrup composition (Samples H) within the scope of this invention was prepared comprising 97.5% of the cough syrup base formulation above and 2.5% of the flavoring composition Sample A prepared in Example I. Sample H was compared to a control cough syrup composition comprising a similar cough syrup base and 0.67% chloroform. Sample H was evaluated by an experienced taste panel to have similar taste, mouthfeel and diffusive aroma as the control cough syrup composition containing chloroform.

We claim:

1. A liquid flavoring composition consisting essentially of in an acceptable solvent to about 1.0% by weight of one or more pungent and biting tasting pepper-like constituent(s) and from about 5.0% to about 99.5% by weight of one or more volatile formate ester(s); said composition being substantially free of chloroform and suitable as an orally-consumable chloroform substitute, and having essentially all of the sweet, cooling, tingly, slightly burning and biting taste and mouthfeel characteristics of chloroform.

2. A composition of claim 1 wherein said pepper-like constituents are selected from the group consisting of piperine, iso-piperine, chavicine, iso-chavicine, capsaicin, capsicum extract, capsium oleoresin, zingerone, mustard oil, horseradish extract, hot pepper oil, hot pepper extract, and mixture thereof.

3. A composition of claim 1 wherein said pepper-like constituent is piperine.

4. A composition of claim 1 wherein said volatile formate esters are selected from the group consisting of ethyl formate, methyl formate, propyl formate, isopropyl formate and mixtures thereof.

5. A composition of claim 1 wherein said volatile formate ester is ethyl formate.

6. A composition of claim 1 comprising by weight from about 0.1% to about 0.7% piperine, from about 20% to about 99.4% ethyl formate, from about 0% to about 42% glycerine and from about 0% to about 65% ethyl alcohol.

7. A composition of claim 6 comprising by weight about 0.13% piperine, about 20.77% ethyl formate, about 41.65% glycerin and about 37.45% ethyl alcohol.

8. A composition of claim 6 comprising by weight about 0.62% piperine and about 99.38% ethyl formate.

9. A composition of claim 6 comprising by weight about 0.22% piperine, about 35.6% ethyl formate and about 64.18% ethyl alcohol.

10. A liquid pharmaceutical composition comprising from about 0.05% to about 6% by weight of the composition of claim 1 as an orally-consumable chloroform substitute.

11. A pharmaceutical composition of claim 10 wherein said pharmaceutical composition comprises a cough or cold medicine.

12. A pharmaceutical composition of claim 11 wherein said cough medicine comprises by weight about 11.4 parts sodium citrate, about 3 parts sodium saccharin, about 2 parts sodium benzoate, about 700 parts glucose, about 39.3 parts glycerin, about 2.2 parts citric acid, about 27 parts ammonium chloride, about 2.1 parts sucrose, about 2.8 parts diphenhydramine hydrochloride, about 0.22 parts menthol, about 52.4% parts ethyl alcohol, about 8.1 parts flavoring and about 25 parts of said chloroform substitute flavoring composition.

13. An oral hygiene composition comprising from about 0.01% to about 5% by weight of the composition of claim 1 as an orally-consumable chloroform substitute.

14. An oral hygiene composition of claim 13 wherein said oral hygiene composition is a mouthwash.

15. An oral hygiene composition of claim 13 wherein said oral hygiene composition is toothpaste.

16. A method for improving the taste of an orally-consumable liquid material comprising uniformly incorporating therein, as a chloroform substitute, from about 0.01% to about 6% by weight of the flavoring composition of claim 1.

17. The method of claim 16 wherein said pepper-like constituents are selected from the group consisting of piperine, iso-piperine, chavicine, iso-chavicine, capsaicin, capsicum extract, capsicum oleoresin, zingerone, mustard oil, horseradish extract, hot pepper oil, hot pepper extract, and mixtures thereof.

18. The method of claim 16 wherein said pepper-like constituent is piperine.

19. The method of claim 16 wherein said volatile formate esters are selected from the group consisting of ethyl formate, methyl formate, propyl formate, isopropyl formate and mixtures thereof.

20. The method of claim 16 wherein said volatile formate ester is ethyl formate.

21. The method of claim 19 wherein said orally-consumable liquid material is a pharmaceutical composition.

22. The method of claim 21 wherein said pharmaceutical composition is a cough or cold medicine.

23. The method of claim 16 wherein said orally-consumable material is a mouthwash.

24. The method of claim 16 wherein said orally-consumable material is toothpaste.

* * * * *